United States Patent [19]
Umitsuki et al.

[11] Patent Number: 6,127,161
[45] Date of Patent: Oct. 3, 2000

[54] LEUCINE AMINOPEPTIDASE GENE, RECOMBINANT DNA, AND PROCESS FOR PRODUCING LEUCINE AMINOPEPTIDASE

[75] Inventors: Genryou Umitsuki, Chiba; Keietsu Abe, Miyagi, both of Japan

[73] Assignee: Kikkoman Corporation, Chiba, Japan

[21] Appl. No.: 09/330,095

[22] Filed: Jun. 11, 1999

[30] Foreign Application Priority Data

Jun. 12, 1998 [JP] Japan .................................. 10-164611

[51] Int. Cl.$^7$ .............................. C12N 9/48; C12N 1/20; C12N 15/00; C12N 15/57; C07H 21/04
[52] U.S. Cl. ........................ 435/212; 435/320.1; 435/325; 435/252.3; 536/23.2
[58] Field of Search ............................ 435/6, 212, 320.1, 435/325, 252.3; 536/23.2

[56] References Cited

FOREIGN PATENT DOCUMENTS

| 51-9035 | 3/1976 | Japan . |
| 98/51803 | 11/1998 | WIPO . |
| WO 98/51804 | 11/1998 | WIPO . |

*Primary Examiner*—Rebecca E. Prouty
*Attorney, Agent, or Firm*—Finnegan, Henderson, Farabow, Garrett & Dunner, L.L.P.

[57] ABSTRACT

The present invention relates to an Aspergillus sojae leucine aminopeptidase gene or variants thereof, a recombinant DNA including the gene or the variants, and a process for producing leucine aminopeptidase using the recombinant DNA.

7 Claims, 1 Drawing Sheet

LEUCINE AMINOPEPTIDASE GENE, RECOMBINANT DNA, AND PROCESS FOR PRODUCING LEUCINE AMINOPEPTIDASE

TECHNICAL FIELD OF THE INVENTION

The present invention relates to a leucine aminopeptidase gene, recombinant DNA, and a process for producing leucine aminopeptidase.

BACKGROUND OF THE INVENTION

Leucine aminopeptidase is a hydrolase that acts on a partially hydrolyzed protein, thereby cleaving a peptide bond at the N-terminus of the protein, and this enzyme plays an important role in producing food products such as seasonings. In particular, leucine aminopeptidase derived from filamentous fungi is very important since it exerts a suitable reactivity for producing seasonings.

Until now, the structure of leucine aminopeptidase gene from filamentous fungi, however, was unknown at all. In fact, the gene has not yet been isolated.

Thus, the object of the present invention is to isolate a leucine aminopeptidase gene, to obtain a transformant prepared with the gene, and to provide a process for producing leucine aminopeptidase through the culture of the transformant.

SUMMARY OF THE INVENTION

The present inventors have now succeeded in isolating a leucine aminopeptidase gene, preparing a transformant using the gene, and establishing a process for efficiently producing the leucine aminopeptidase by the transformant.

According to one aspect of the invention, a leucine aminopeptidase gene is provided which encodes the following protein (a) or (b): (a) a protein having an amino acid sequence shown in SEQ ID NO:1; or (b) a protein with leucine aminopeptidase activity comprising one or more deletions, substitutions or additions in the amino acid sequence of (a).

According to another aspect of the invention, a leucine aminopeptidase gene is provided which comprises the following DNA (a) or (b) : (a) a DNA having a nucleotide sequence shown in SEQ ID NO:2; or (b) a DNA encoding a protein with leucine aminopeptidase activity which hybridizes with a complementary sequence of the DNA having a nucleotide sequence of (a) under stringent conditions.

In still another aspect of the invention, a recombinant DNA is provided in which the above-described leucine aminopeptidase gene has been inserted into a vector DNA.

In yet still another aspect of the invention, there is provided a host cell transformed with the DNA containing the above-described leucine aminopeptidase gene. The host cell is a so-called transformant.

The present invention further provides a host cell transformed with the above recombinant DNA.

The present invention further provides a process for producing leucine aminopeptidase, comprising the steps of: culturing the above-described host cell in a medium; and recovering leucine aminopeptidase from the medium.

DETAILED DESCRIPTION OF THE INVENTION

Figure 1:
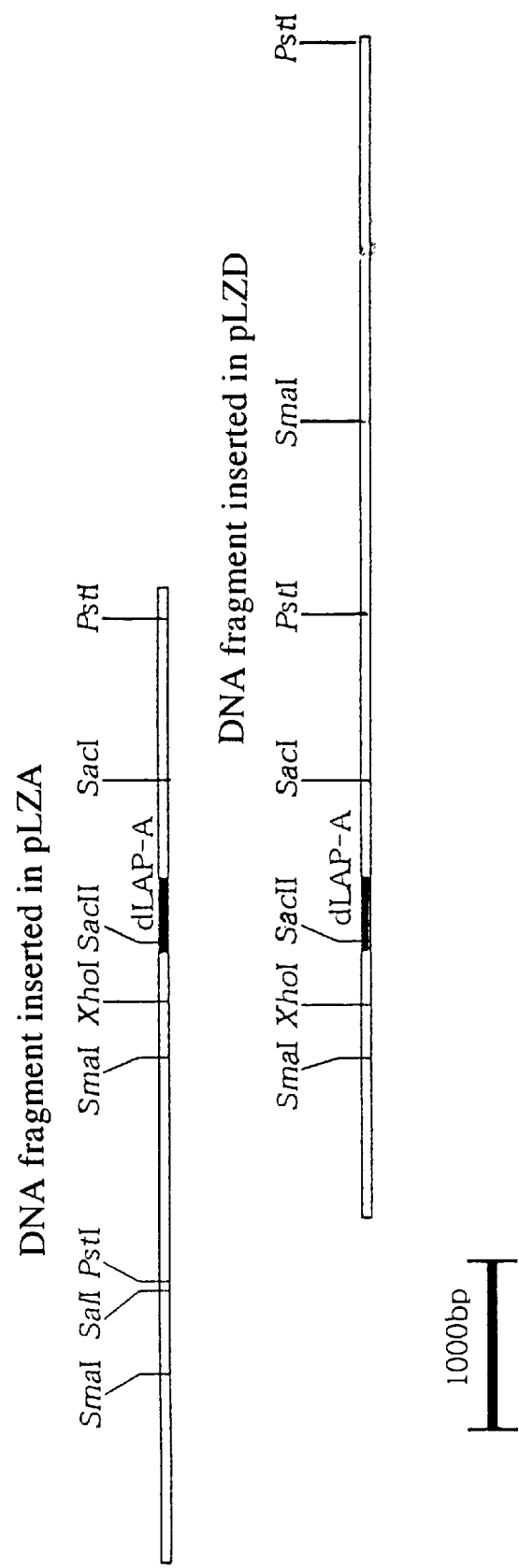
FIG. 1 depicts restriction maps of DNA fragments containing a leucine aminopeptidase gene.

Hereinafter, the present invention will be described in more detail.

Leucine aminopeptidase activity may be determined, for example, by any one of the following three methods.

Method 1: Assay using leucyl-glycyl-glycine (Leu-Gly-Gly) as a substrate

This method frequently invites inaccuracy when a large amount of free amino acids are present in an enzyme solution to produce a high background. In this case, the free amino acids have to be removed from the enzyme solution by dialysis or a spin column such as Centricon (Amicon).

First, the following solutions are prepared.

Solution A: a solution of 1.05 mM Leu-Gly-Gly in 25 mM HEPES, pH8.0 (substrate concentration when reacted: 1 mM)

Solution B: an aqueous solution of 0.4% (w/v) trinitrobenzenesulfonic acid (TNBS)

Solution C: an aqueous solution of 5% (w/v) $Na_2B_4O_7 \cdot 10H_2O$

Solution D: an aqueous solution of 100 mM $CuSO_4$

Solution E: a mix of 250 $\mu$l of Solution B, 975 $\mu$l of

Solution C and 25 $\mu$l of Solution D per specimen (prepared upon use)

Then, two microcentrifuge tubes per specimen are each filled with 25 $\mu$l of the enzyme solution. One of the two tubes is heated at 100° C. for 5 min. to inactivate the enzyme for use as a blind test sample. To each microcentrifuge tube, 475 $\mu$l of Solution A (at 30° C.) is added and stirred prior to carrying out the enzyme reaction at 30° C. for 10–60 min. The reaction is terminated by heating at 100° C. for 5 min. To the reaction mixture, 625 $\mu$l of Solution E (at 37° C.) is added and stirred. After keeping the mixture at 37° C. for 25 min., an absorbance is measured at 420 nm. Providing that 1 unit equals to an activity for freeing 1 $\mu$mol of Leu per min. from Leu-Gly-Gly, the leucine aminopeptidase activity can be calculated by the following equation:

$$\text{Activity (unit/ml)} = (\Delta OD \times 0.125 \times 1,000)/(25 \times T)$$

wherein $\Delta OD$ is obtained by subtracting an OD value of the blind test sample from an OD value of the test sample; and T is a reaction time (in min.).

Method 2: Assay using L-leucine-p-nitroanilide (Leu-pNA) as a substrate

First, the following solutions are prepared:

Solution A: 100 ml of 1 mM Leu-pNA solution which is obtained by dissolving 0.1 mmol of Leu-pNA in 5 ml of ethanol and then adding 10 ml of 500 mM Tris buffer (pH 8.5) and 85 ml of distilled water Solution B: 0.1 N HCl Then, a microcentrifuge tube containing 30 $\mu$l of the enzyme solution and a blank microcentrifuge tube for blind test are each filled with 300 $\mu$l of Solution A and stirred prior to carrying out the enzyme reaction at 30° C. for 10–60 min. 900 $\mu$l of Solution B is added and stirred in order to terminate the enzyme reaction. To the microcentrifuge tube for blind test, 30 $\mu$l of the enzyme solution is added and stirred. An absorbance is determined at 400 nm. Providing that 1 unit equals to an activity for freeing 1 $\mu$mol Leu per min. from Leu-pNA, the leucine aminopeptidase activity can be calculated by the following equation:

$$\text{Activity (unit/ml)} = (\Delta OD \times 0.69 \times 1,000)/(30 \times T)$$

wherein $\Delta OD$ is determined by subtracting an OD value of the blind test sample from an OD value of the test sample; and T is a reaction time (in min.).

Method 3: Simple assay for detecting abilities of various strains to produce leucine aminopeptidase Solutions A and B in Method 2 are used as reagents.

Ten μl of sterilized distilled water, or an aqueous solution of 0.01% (w/v) Tween-20, containing about 1,000 spores from a filamentous fungous, e.g., Koji mold *Aspergillus sojae,* is applied to a thick paper disk (8 mm φ; Toyo Roshi Co., Ltd.) placed on a soybean powder agar medium [3% (w/v) defatted soybean powder obtained by swelling under heat and pressure conditions, 1% (w/v) $KH_2PO_4$, 1.5% agar powder, pH6.0]. A blind test is concurrently conducted in the same manner, except that there are contained no spores. They are cultured at 30° C. until sporulation begins (for about 48 hours in the case of Koji). Each paper disk with the cell is transferred to a test tube (10 mm diameter or larger), to which 600 μl of Solution A is added at 30° C. The mixture is then thoroughly stirred prior to carrying out the enzyme reaction at 30° C. for 7–30 min. Then, to the reaction mixture, 600 ml of Solution B is added and vigorously stirred, after which an absorbance is determined at 400 nm. The arbitrary unit of the leucine aminopeptidase activity is determined by subtracting an absorbance of the blind test sample from that of the test sample. However, since this method gives widely varied results, it is desirable to conduct three or more simultaneous tests per strain. Moreover, strains that are to be compared to each other should be subjected to simultaneous assay. When an organism other than filamentous fungi is used, it may be assayed in a similar way by suitably modifying the number of cells, a medium composition, and a culture time.

The donor of the gene of the present invention is, for example, *Aspergillus sojae* 1-190 (FERM BP-6349) or the like.

The above-mentioned microorganisms may be cultured according to a general cultivation method of filamentous fungi (which is referred to as the method described in JP-A-48-35094) to produce and purify leucine aminopeptidase.

The thus-obtained leucine aminopeptidase is fragmented under denaturation conditions with a lysylendpeptidase (Wako Pure Chemical Industries, Ltd., Osaka, Japan). The fragments are separated by reversed-phase high-performance liquid chromatography using, for example, POROS R2/H Prepacked Column (Boehringer Mannheim) for sequencing amino acid sequences of the separated peptide fragments by using, for example, ABI470A Protein Sequencer (Perkin-Elmer).

Based on the determined amino acid sequences, PCR primers are prepared while taking degeneracy of codon into consideration and are used as mixed primers. Where all of the four bases are degenerate, inosine may be used. PCR reaction is performed using the prepared primers with chromosomal DNA of the donor (e.g., *Aspergillus sojae* 1–190 (FERM BP-6349)) as a template. The chromosomal DNA of *Aspergillus sojae* 1–190 (FERM BP-6349) may be obtained according to the method of Joan Tilburn et al.: Gene, 26, 205–221 (1983). The annealing temperature for the PCR is determined using Robocycler Gradient (Stratagene). For example, Ex Taq DNA polymerase (Takara Shuzo, Co. Ltd., Kyoto, Japan) may be used for the PCR. The amplified DNA fragments are independently inserted into a vector DNA such as pGEM-T Easy plasmid (Promega) to obtain recombinant plasmids. The nucleotide sequences of the DNAs inserted into the plasmid are determined by using, for example, Model4200 DNA sequencer (Li-COR Inc.) or the like in order to select DNA having, at its both ends, nucleotide sequences correctly encoding the amino acid sequences of the peptides used for designing the PCR primers.

The selected DNA fragment is labeled, and it is used to isolate clones with the gene of interest through plaque hybridization from a phage library containing chromosomal fragments of *Aspergillus sojae.* The phage library may be prepared, for example, by using ZAP Express Vector Kit (Stratagene). The labelling of the DNA fragment and the detection of hybridization may be conducted using, for example, DIG DNA labeling/detecting system (Boehringer Mannheim).

From the isolated phage clones, plasmids are prepared according to the instructions appended to the kit. The several plasmids are fragmented with restriction enzymes so as to prepare a restriction map. Based on the restriction map, subcloning plasmids containing the respective insert fragments are prepared and determined for their nucleotide sequences as described above. The thus-determined nucleotide sequences are analyzed to determine the nucleotide sequence coding for the polypeptide of interest (shown in SEQ ID NO:2), then the amino acid sequence therefor, i.e., the amino acid sequence shown in SEQ ID NO:1.

Various known methods may be employed to obtain genes coding for leucine aminopeptidase variants with leucine aminopeptidase activity and with one or more, preferably several deletions, substitutions or additions of amino acids in the amino acid sequence shown in SEQ ID NO: 1. Methods usable for the purposes include, for example, a well-known site-directed mutagenesis for point mutation or deletion mutation of genes; a method which includes selective cleavage of genes, removal or addition of selected nucleotides, or ligation of genes; and an oligonucleotide-directed mutagenesis.

It is highly probable that the so-obtained DNA encodes a polypeptide responsible for leucine aminopeptidase activity. Using the DNA, transformation may be performed and the resultant may be selected for the activity of interest as described below.

Genes substantially identical to the leucine aminopeptidase gene of the invention may be obtained by hybridization under stringent conditions with a DNA having the nucleotide sequence shown in SEQ ID NO:2, a complementary strand thereof, or a probe comprising part of the nucleotide sequence or the complementary strand, then by selection of those encoding polypeptides with leucine aminopeptidase activity. The term "stringent conditions" as used herein refers to conditions in which only a specific hybrid is selectively formed and detected for its signal, whereas non-specific hybrid is not formed. These conditions may slightly vary depending on types of organisms but can readily be determined by examining salt concentrations and temperatures upon hybridization and washing by common methods. For example, a specific signal can be observed under the conditions described later in (6) of Example 1 in which hybridization is performed using 5×SSC, 1.0% (w/v) nucleic acid hybridization blocking reagent (Boehringer Mannheim), 0.1% (w/v) N-lauroyl sarocosine and 0.02% (w/v) SDS overnight (about 8–16 hours), followed by two washings using 0.1×SSC and 0.1% (w/v) SDS for 15 min each. The temperatures of the hybridization and washing are independently 45° C. or higher, preferably 52° C. or higher, more preferably 57° C. or higher. It is highly probable that DNAs that hybridize under such conditions encode peptides with leucine aminopeptidase activity. Among the DNAs, however, there may exist a DNA that loses its leucine aminopeptidase activity through mutation. In this case, following transformation, any DNA without the activity can easily be removed away by determining an ability of a transformant to produce leucine aminopeptidase according to Method 3 above developed by the present inventors.

The thus-obtained leucine aminopeptidase genes can be used to transform host cells such as bacteria, fungi, yeasts, insect cells, plant cells or animal cells, preferably filamentous fungi, for example, Aspergillus sojae ATCC42251 according to methods described in J. Sambrook et al., Molecular Cloning, Second Edition, Cold Spring Harbor Laboratory Press, 1989; E. Shiela et al., Molecular & General Genetics, 218, 99–104 (1989); etc. In the transformation method in which a filamentous fungous is used as a host cell, the cultured cell is treated with a cell-wall degrading enzyme such as Novozym 234 (Novo Nordisk A/S) to obtain a protoplast in which the cell-wall has been removed. Then, DNA containing a marker gene such as niaD, and DNA containing a gene of interest, are concurrently introduced into the protoplast in the coexistence of calcium chloride and polyethyrene glycol 4000. Thereafter, the so-treated protoplast is diluted in a selection medium suitable for the used marker gene and then is kept warm, whereby a transformant in which both the marker gene and the gene of interest have been integrated in the chromosome of the host cell can be regenerated. The leucine aminopeptidase gene may be a recombinant DNA inserted into a vector, or a non-recombinant DNA such as a DNA fragment amplified from a chromosomal DNA by PCR. In the latter case, transformation can be performed without troubles because even the non-recombinant DNA can be integrated in the chromosome of a host cell. The obtained transformants may be screened for an enhanced ability to produce leucine aminopeptidase as measured by, for example, Method 3 described above, to obtain a transformant of interest.

The thus-obtained transformant can be cultured according to the method described in JP-A-48-35094 to produce and purify leucine aminopeptidase, resulting in efficient production of leucine aminopeptidase.

EXAMPLES

Hereinafter, the present invention will be illustrated in more details by the following non-limited examples.

Example 1

Cloning of Leucine Aminopeptidase Gene (1) Purification of enzyme

Koji mold *Aspergillus sojae* 1-190 (FERM BP-6349) was cultured to produce and purify leucine aminopeptidase as described above (3 mg yield).

(2) Determination of partial amino acid sequence 30 ng of the purified enzyme was used as a sample and the N-terminal amino acid sequence thereof was determined to be Gly Arg Ala Leu Val Ser Pro Asp Glu Phe Pro (SEQ ID NO:3) by using ABI470A Protein Sequencer (Perkin-Elmer). However, since this enzyme allows an amino acid to be released from the N-terminus of a peptide, it was impossible to avoid contaminants partially lacking the N-terminus by autolysis, resulting in that no sequence other than the above-determined sequence was obtained.

Instead, the enzyme was fragmented with lysylendpeptidase (Wako Pure Chemical Industries, Ltd., Osaka, Japan) to determine its internal amino acid sequence. There, however, still remained the problem of amino acids release from the N-termini of peptide fragments due to the remaining enzyme activity.

Through further examinations, the present inventors have found that the enzyme was fragmented under such conditions that inactivate the enzyme but allows lysylendpeptidase to function. First, 1 mg of the purified enzyme was inactivated at 37° C. for 1.5 hours in 0.5 ml of 50 mM Tris-buffer (pH 9.0) containing 1% (w/v) SDS and 5 mM EDTA. After the inactivation, 15 µl of 0.1 mg/ml lysylendpeptidase (Wako Pure Chemical Industries, Ltd., Osaka, Japan) was added for the reaction at 37° C. for 14 hours. Five µl of the lysylendpeptidase was further added to continue the reaction at 37° C. for 2 hours. The thus-obtained solution containing peptide fragments was added to 55 µl of 1 M potassium phosphate buffer (pH 7.5), left on ice for 30 min., and centrifuged at 15,000×g for 20 min. to remove SDS. From this peptide fragment solution, solid substance was removed using Column Guard HV 13 mm (Millipore). To 100 µl of the prepared peptide fragment solution, trifluoroacetic acid (hereinafter referred to as "TFA") was added to a final concentration of 0.1% in order to perform a reversed-phase chromatography with a gradient from 0 to 47.5% acetonitrile in 0.1% TFA-containing ultrapure water using POROS R2/H Pre-packed Column (Boehringer Mannheim). Each peptide peak was fractionated monitoring an absorbance at 220 nm as the indication. The peptide solution obtained at each peak was evaporated to dry with a vacuum centrifugal concentration system, and re-dissolved in 20 µl of 20 mM phosphate buffer (pH 8.0). Amino acid sequences of these peptides were determined using ABI470A Protein Sequencer (Perkin-Elmer). As a result, peptide at Peak 5 was Xaa Xaa Xaa Xaa Xaa Xaa Xaa Asp Tyr Pro Ser Val Glu Gly Lys (where Xaa is an amino acid that was unable to be identified due to contamination of other peptide) (SEQ ID NO:4); peptide at Peak 6 was Gln Pro Gln Val His Leu Trp . . . (SEQ ID NO:5); and peptide at Peak 11 was Asn Ala Val Arg Phe Leu Phe Trp Thr Ala Glu Glu Phe Gly Leu Leu Gly Ser Asn Tyr Tyr Val Ser His Leu . . . (SEQ ID NO:6).

(3) Preparation of parts of leucine aminopeptidase gene by PCR

PCR primers were designed based on the partial amino acid sequences determined in (2) above.

Based on Peak 5, LAP5F (5'- GA(C/T)TA(C/T)CCI(A/T)(C/G)IGA(C/T)GTIGA(A/G)GGIAAG-3'; SEQ ID NO:7) and LAP5R (5'- TTICC(C/T)TCIAC(A/G)TCI(C/G)(A/T) IGG(A/G)TA(A/G)TC-3'; SEQ ID NO:8) were prepared. Based on Peak 11, LAP11F (5'- TT(C/T)TGGACIGCIGA(A/G)GA(A/G)TT(C/T)GG-3'; SEQ ID NO:9) and LAP11R (5'-CC(A/G)AA(C/T)TC(C/T)TCIGCIGTCCA(A/G)AA-3'; SEQ ID NO:10) were prepared. "I" refers to "inosine". Parts of the leucine aminopeptidase gene were amplified by PCR as described below while using the above primer sets and the genomic DNA from *Aspergillus sojae* 1-190 (FERM BP-6349), as a template, which was prepared according to the method of Joan Tilburn et al., Gene, 26, 205–221 (1983). A thermocycler used was RoboCycler Gradient 96 (Stratagene), and ExTaq (Takara Shuzo Co., Ltd., Kyoto, Japan) was used as a PCR reagent.

33.75 µl of sterilized distilled water, 5 µl of 10×buffer (as a component of ExTaq), 2 µl each of the two primer DNA solutions (100 pmol/µl), 3 µl of 0.5 µg/µl genomic DNA solution, 4 µl of 2.5 mM dNTP solution (Takara Shuzo, Co., Ltd., Kyoto, Japan) and 0.25 µl of ExTaq DNA polymerase were put and mixed in a 0.2-ml PCR tube (Ina Optica, T-02). 20 µl of mineral oil (Sigma) was added dropwise to the mixture before setting the tube in RoboCycler Gradient 96. The genomic DNA was previously denatured at 96° C. for 3 min., then rapidly cooled on ice. The primers consisted of either combination of LAP5F and LAP11R or LAP5R and LAP11F. The reaction was conducted while programming the RoboCycler Gradient 96 as follows: (i) 95° C., 30 sec.; 45 cycles of (ii) 95° C., 30 sec., (iii) 36–56° C., 30 sec. and (iv) 72° C., 2 min.; and thereafter (v) 72° C., 5 min. The step (iii) was performed by setting the temperature of the annealing block to have a gradient from 36 to 58° C. and by placing tubes therein, where the set temperatures were 36° C., 40° C., 44° C., 48° C., 52° C. and 56° C. After the reaction, 5 µl of the reaction mixture was electrophoresed on 0.7% agarose LO3 gel (Takara Shuzo, Co., Ltd., Kyoto, Japan) to confirm amplified products. A product of about 500 bp was mainly amplified in the reaction mixture obtained with the primers LAP5F and LAP11R, and a product of about 1,200 bp in the reaction mixture obtained with the primers LAP5R and LAP11F. The optimal annealing temperature was 48° C.

40 µl each of the reaction mixtures (annealing temperature 48° C.) were electrophoresed on 2% agarose gel to recover the two amplified products from the gels. DNAs were recovered from the gels using QIAquick Gel Extraction kit (Qiagen GmbH) by elution from the spin column with 25 µl of sterilized distilled water. Using 7 µl each of the two DNA fragment solutions, each of the DNA fragments was introduced into pGEM-T Easy plasmid (Promega) according to the manual of pGEM-T Easy Vector System II (Promega). The resulting plasmids were then used to transform *E.coli* JM109 competent cell (which is a component of the kit).

From the obtained transformants (4 strains each), recombinant plasmids were prepared according to Molecular Cloning 2nd edition, 1.25–1.28, Cold Spring Harbour Laboratory Press (1989). The nucleotide sequences of these plasmids were determined using Thermo Sequenase Cycle Sequencing kit (Amersham) on Model4200 DNA Sequencer (Li-COR Inc.). Of the four recombinant plasmids with the 500 bp fragment, two plasmids had, at their ends, nucleotide sequences encoding the amino acid sequences used for designing the primers. The internal nucleotide sequence did not contain a stop codon in the reading frame for the above amino acid sequence. Therefore, the fragment was expected to be part of the leucine aminopeptidase gene of interest. This plasmid was named pCRLA.

(4) Preparation of Koji genomic DNA library

Genomic DNA of koji *Aspergillus sojae* 1-190 (FERM BP-6349) was prepared as described in (3) above and was subjected to limited cleavage with Sau3AI such that the average base number of DNA fragments was around 10 kbp. The around 10 kbp DNAs were collected by agarose gel electrophoresis using QIAquick, then introduced into ZAP Express vector using ZAP Express Predigested Gigapack III Cloning Kit (Stratagene). Following packaging and amplification, λ phage library of the genomic DNA was obtained.

(5) Preparation of DNA probe

Based on the presumed partial nucleotide sequence of the leucine aminopeptidase gene obtained in (3) above, two kinds of primers: FOW-LAP-A 5'-AGGGCAAGGTAGCTCTCATCAAGCGTGG-3' (SEQ ID NO:11) and REV-LAP-A 5'-GAGAAAGCGCACGGCATTCTTGACGGAG-3' (SEQ ID NO:12) were prepared. Part of the leucine aminopeptidase gene was amplified by PCR using LAP5F and LAP11R as primers and 10 ng of pCRLA as a template under conditions set forth below:

34.75 µl of sterilized distilled water, 5 µl of 10×buffer, 2 µl each of two primer DNA solutions (100 pmol/µl), 2 µl of 5 ng/µl genomic DNA solution, 4 µl of 2.5 mM dNTP solution and 0.25 µl of ExTaq DNA polymerase were put and mixed in a 0.2-ml PCR tube. 20 µl of mineral oil was then added dropwise to the mixture before setting the tube in RoboCycler Gradient 96. The genomic DNA was in advance denatured at 96° C. for 3 min., then rapidly cooled on ice. The reaction was conducted while programming the RoboCycler Gradient 96 as follows: (i) 95° C., 30 sec.; 45 cycles of (ii) 95° C., 30 sec., (iii) 50° C., 30 sec. and (iv) 72° C., 40 sec.; and thereafter (v) 72° C., 2 min. The reaction mixture was electrophoresed on 1% agarose gel to recover an amplified fragment of about 500 bp using QIAquick Gel Extraction kit (Qiagen). The amplified fragment was eluted with 50 µl of TE buffer (10 mM Tris, 1 mM EDTA, pH 8.0).

Digoxigenin (DIG)-labeled DNA probe was prepared through PCR as follows, using FOW-LAP-A and REV-LAP-A as primers and a 10-fold dilution of the above amplified fragment solution as a template: 37.75 µl of sterilized distilled water, 5 µl of 10×buffer, 1 µl each of the two primer DNA solutions (100 pmol/µl), 1 µl of template DNA solution, 4 µl of 10×PCR DIG mix (Boehringer Mannheim) and 0.25 µl of ExTaq DNA polymerase were put and mixed in a 0.2-ml PCR tube. 20 µl of mineral oil was added dropwise to the mixture before setting the tube in RoboCycler Gradient 96. The genomic DNA was previously denatured at 96° C. for 3 min., then rapidly cooled on ice. The reaction was conducted while programming the RoboCycler Gradient 96 as follows: (i) 95° C., 30 sec.; 45 cycles of (ii) 95° C., 30 sec., (iii) 62° C., 30 sec. and (iv) 72° .C, 40 sec.; and thereafter (v) 72° C., 2 min. The amplified fragment was collected from the reaction mixture by ethanol precipitation, and dissolved in 50 µl of TE buffer. This was named as DIG-labeled probe dLAP-A.

(6) Screening of leucine aminopeptidase gene by plaque hybridization

The λ phage library of the Koji genomic DNA prepared in (4) was screened for the leucine aminopeptidase gene by using the probe of (5).

According to the instructions appended to the kit for preparing the library, approximately $5 \times 10^3$ of plaques per plate were formed on 5 agar medium plates. From each plate, the DNA was transferred to HyBond-N+ Nylon Transfer Membrane (Amersham) according to the instructions appended to the membrane. In this case, for elimination of non-specific signals, the DNA was transferred to two membranes per plate individually.

Those membranes were subsequently subjected to hybridization and detection by using the digoxygenin-labeled DNA probe prepared in (5) and DIG system (Boehringer Mannheim) according to "Users Guide for hybridization using DIG system", pages 37–40, Boehringer Mannheim (1996). Specifically, a standard pre-hybridization buffer (5×SSC, 1% (w/v) nucleic acid hybridization blocking reagent (Boehringer Mannheim), 0.1% (w/v) N-lauroyl sarcosine, and 0.02% (w/v) SDS) was applied to each of the above ten membranes on which the DNAs of the phage library have been adsorbed, and the membranes were left at 57° C. for 1 hour while shaking gently.

Thereafter, the dLAP-A probe prepared in (5), which has been heated at 100° C. for 10 min and rapidly cooled in ice water, was applied to each membrane which was then left at 57° C. for 16 hours while shaking gently. Each membrane was transferred to a new container and washed twice with 2×washing solution (2×SSC, 0.1% (w/v) SDS) at room temperature for 5 min., and subsequently washed twice with 0.1×washing solution (2×SSC, 0.1% (w/v) SDS) at 57° C. for 15 min. Each membrane was then equilibrated with Buffer 1 (0.1 M maleic acid, 0.15 M NaCl, pH 7.5) for 1 min., and transferred to a new container, to which Buffer 2 (Buffer 1, 1% (w/v) nucleic acid hybridization blocking reagent) was added, followed by gently shaking at room temperature for 30 min. After discarding Buffer 2, an alkaline-phosphatase-labeled anti-digoxygenin antibody diluted 1:10,000 with Buffer 2 was added and gently shaken at room temperature for 30 min. After discarding the antibody solution, the membranes were individually washed twice with Buffer 1 containing 0.3% Tween 20 in a clean container. Then, they were equilibrated with Buffer 3 (0.1M Tris pH9.5, 0.1 M NaCl, 50 mM $MgCl_2$) for 2 min. Each of the membranes was placed in a hybridization bag cut into a suitable size, to which 0.4 ml of 100-fold diluted CDP-Star solution (Boehringer Mannheim) was added dropwise, thereby being uniformly distributed over the membrane. After removal of the excessive solution, the bags were sealed with a sealer. These membranes were kept at 37° C. for 10 min. and then closely attached to Fuji direct photography films RX-U (Fuji Photo Film Co., Ltd.) for 1–10 min., which films were then developed. Five signals (named Signals A to E) were observed at the same location on the two membranes to which the plaques on the same agar medium plate have been transferred. A to E might be positive clones. Soft agar portions (5 mm diameter) were removed from the positions corresponding to Signals A to E and put in respective microcentrifuge tubes. After 500 µl of SM buffer (10 mM NaCl, 0.2% (w/v) $MgSO_4.7H_2O$, 50 mM Tris pH7.5, 0.01% gelatin) and 20 µl of chloroform were added, the tubes were left at 4° C. overnight. While being controlled such that about 100 phages per tube were produced, plaques were formed on these agar media. They were transferred to respective membranes as described above in order to perform hybridization with dLAP-A probe. For the phage solution obtained from Signal A, a number of strong signals were observed. While no signal was observed for Signal B, a few signals were observed for Signals C, D and E. Plaques were collected from Signals A, C, D and E as described above to perform plaque hybridization again. Since all plaques of Signals A and D turned out to be positive, single plaques were recovered individually from Signals A and D.

The phage clones of Signals A and D were subjected to in vitro excision according to the instructions appended to the kit to obtain their plasmids, which were named pLZA and pLZD, respectively.

(7) Analysis of leucine aminopeptidase gene

The two plasmids obtained in (6) were analyzed. First, PCR was conducted using these plasmids as templates. FOW-LAP-A, REV-LAP-A, and primers for both sides of the cloning site of the vectors, i.e., F: 5'-CGACGTTGTAAAACGACGGCCAGT-3' (SEQ ID NO:12) and R: 5'-GAGCGGATAACAATTTCACACAGG-3' (SEQ ID NO:13), were used in the following combinations:

(a) FOW-LAP-A and F
(b) REV-LAP-A and F
(c) FOW-LAP-A and R
(d) REV-LAP-A and R

The conditions for the PCR were the same as those for preparing dLAP-A except that the elongation reaction was performed at 72° C. for 8 min. The PCR products were subjected to agarose gel electrophoresis. For those obtained with the PLZA template, about 2.1 kbp and about 4.1 kbp bands were observed with the primer combinations (a) and (d), respectively. For those obtained with the PLZD template, about 2 kbp band was observed with the primer combination (d).

These plasmids were cleaved with restriction enzymes according to a routine method, and subjected to agarose gel electrophoresis to prepare a brief restriction enzyme map. The restriction map was combined with the results of the PCR and, based on this information, a possible location of the leucine aminopeptidase gene was presumed (FIG. 1). As a result, pLZA and pLZD were presumed to contain the same DNA fragment comprising the leucine aminopeptidase gene.

The DNA fragment on pLZA was suitably subcloned to determine its nucleotide sequence by the method described in (3). A sequence that could not be determined by this method was determined with Dye Terminator Cycle Sequencing FS Ready Reaction Kit (Perkin-Elmer) on Model373A Sequencer (Perkin-Elmer). The determined nucleotide sequence is shown in SEQ ID NO:2. Nucleotides 67–171 of SEQ ID NO:2 revealed to be intron based on the sequences at its both ends and the N-terminal sequence of the purified leucine aminopeptidase. The amino acid sequence of mature leucine aminopeptidase, shown in SEQ ID NO:1, was determined based on the amino acid sequence of a polypeptide translated from the combination of nucleotides 1–66 and 172–1640 of SEQ ID NO:2 and the N-terminal sequence of the purified leucine aminopeptidase.

The amino acid sequence of SEQ ID NO:1 was found to be the amino acid sequence of the mature leucine aminopeptidase because it included at the N-terminus the N-terminal sequence of the purified leucine aminopeptidase, and internally the entire internal sequence of leucine aminopeptidase determined in (2). pLZA was concluded to be a vector DNA incorporating the leucine aminopeptidase gene.

Example 2

Preparation of Transformant With Leucine Aminopeptidase Gene

First, a niaD-defective strain was prepared from *Aspergillus sojae* ATCC42251 as a host according to the method described by E. Shiela et al. in Molecular and General Genetics, 218, 99–104 (1989).

pLZA plasmid, i.e. vector DNA into which the leucine aminopeptidase gene has been incorporated, and pSTA14 plasmid into which niaD gene as a marker has been incorporated (E. Shiela et al., supra), were prepared in large amounts using QIAGEN Plasmid Maxi Kit (QIAGEN).

These plasmids were used to transform the niaD-defective strain from *Aspergillus sojae* ATCC42251 according to the method described by E. Shiela (supra), thereby obtaining 25 colonies of the transformants on a minimum medium.

The ability of the obtained transformants to produce leucine aminopeptidase was determined by Method 3 described above. Those having abilities to produce leucine aminopeptidase in the same level, a slightly enhanced level and a greatly enhanced level compared to that of the host strain were selected and were named TFLW14, TFLW5 and TFLW22, respectively.

The obtained *Aspergillus sojae* (TFLW22) was deposited with the National Institute of Bioscience and Human-Technology, Agency of Industrial Science and Technology (1-3, Higashi 1-chome, Tsukuba-shi, Ibaraki-ken, 305, Japan) as the Accession No. FERM BP-6348.

Genomic DNAs of the host strain and the above-described 3 transformant strains were prepared as described in (4) of Example 1, cleaved with the restriction enzyme SalI and blotted onto HyBond-N+ Nylon Transfer Membranes (Amersham). The membranes were examined for copy number of the leucine aminopeptidase gene by hybridization as described in (6) of Example 1 using dLAP-A as a probe. The copy number of the leucine aminopeptidase gene in the host strain, TFLW14, TFLW5 and TFLW22 turned out to be 1, 1, 2–3 and about 10 or more, respectively.

Example 3

Production of Leucine Aminopeptidase Using Transformant 2.78 g of wheat bran and 2.22 ml of distilled water were mixed, put in a 150-ml Erlenmeyer flask, autoclaved at 121° C. for 50 min., and left to cool to room temperature. $10^6$ spores each of the host strain and the three transformant strains were inoculated into respective flasks and left at 30° C. for 24 hours. The flasks were vigorously shaken to break the contents into small particles, which were left at 30° C. for another 48 hours for growth of the cells. 25 ml of distilled water was added to the flasks which were then vigorously shaken and left at room temperature for 3 hours. Enzymes were extracted from the mixtures, thereby obtaining enzyme solutions.

In order to determine aminopeptidase activities of the enzyme solutions, free amino acids and low-molecular peptides were removed from the enzyme solutions. Specifically, 2 ml of each enzyme solution was put in Centricon-10 (Amicon) and centrifuged at 3,000×g. When the amount of the liquid became 0.5 ml, 1.5 ml of 25 mM HEPES buffer (pH 7.0) was added thereto and the mixture was centrifuged three times at 3,000×g. The volume of the collected enzyme solution was adjusted to 2 ml with 25 mM HEPES buffer (pH 7.0).

The leucine aminopeptidase activities of the thus-obtained enzyme samples were determined using Leu-Gly-Gly as a substrate (Table 1). Defining the activity of the host strain as 1, the activities of TFLW14, TFLW5 and TFLW22 were about 1.0, about 2.1 and about 4.9, respectively. Leucine aminopeptidase was efficiently produced by growing the transformant TFLW22 transformed with the vector containing the leucine aminopeptidase gene, as compared to the host strain.

TABLE 1

|  | Leucine aminopeptidase activity (U/g Koji) | Ratio of activity to that of host strain |
| --- | --- | --- |
| ATCC42251 niaD- | 1.14 | 1.0 |
| TFLW14 | 1.18 | 1.0 |
| TFLW5 | 2.41 | 2.1 |
| TFLW22 | 5.56 | 4.9 |

According to the present invention, leucine aminopeptidase can efficiently be obtained by culturing, for example, a microorganism containing the recombinant DNA into which the leucine aminopeptidase gene of the invention has been incorporated. Since the gene of the invention may be used as a sample for protein engineering, the present invention is industrially useful.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

All publications including patent applications cited herein are incorporated herein by reference in their entirety.

The following are information on SEQ ID NOS: 1 and 2 described herein:

```
SEQ ID NO:1:

Gly Arg Ala Leu Val Ser Pro Asp Glu Phe Pro Glu Asp Ile Gln Leu
 1               5                  10                  15

Glu Asp Leu Leu Glu Gly Ser Gln Gln Leu Glu Asp Phe Ala Tyr Ala
                20                  25                  30

Tyr Pro Glu Arg Asn Arg Val Phe Gly Gly Lys Ala His Asp Asp Thr
            35                  40                  45

Val Asn Tyr Leu Tyr Lys Glu Leu Lys Lys Thr Gly Tyr Tyr Asp Val
    50                  55                  60

Tyr Lys Gln Pro Gln Val His Leu Trp Ser Asn Ala Asp Gln Thr Leu
65                  70                  75                  80

Lys Val Gly Asp Glu Glu Ile Glu Ala Lys Thr Met Thr Tyr Ser Pro
                85                  90                  95

Ser Val Glu Val Thr Ala Asp Val Ala Val Val Lys Asn Leu Gly Cys
                100                 105                 110

Ser Glu Ala Asp Tyr Pro Ser Asp Val Glu Gly Lys Val Ala Leu Ile
            115                 120                 125

Lys Arg Gly Glu Cys Ala Phe Gly Asp Lys Ser Val Leu Ala Ala Lys
        130                 135                 140

Ala Lys Ala Ala Ala Ser Ile Val Tyr Asn Asn Val Ala Gly Ser Met
145                 150                 155                 160

Ala Gly Thr Leu Gly Ala Ala Gln Ser Asp Lys Gly Pro Tyr Ser Ala
                165                 170                 175
```

-continued

```
Ile Val Gly Ile Ser Leu Glu Asp Gly Gln Lys Leu Ile Lys Leu Ala
            180                 185                 190

Glu Ala Gly Ser Val Ser Val Asp Leu Trp Val Asp Ser Lys Gln Glu
            195                 200                 205

Asn Arg Thr Thr Tyr Asn Val Ile Ala Gln Thr Lys Gly Gly Asp Pro
            210                 215                 220

Asn Asn Val Val Ala Leu Gly Gly His Thr Asp Ser Val Glu Ala Gly
225                 230                 235                 240

Pro Gly Ile Asn Asp Asp Gly Ser Gly Ile Ile Ser Asn Leu Val Val
            245                 250                 255

Ala Lys Ala Leu Thr Gln Tyr Ser Val Lys Asn Ala Val Arg Phe Leu
            260                 265                 270

Phe Trp Thr Ala Glu Glu Phe Gly Leu Leu Gly Ser Asn Tyr Tyr Val
            275                 280                 285

Ser His Leu Asn Ala Thr Glu Leu Asn Lys Ile Arg Leu Tyr Leu Asn
            290                 295                 300

Phe Asp Met Ile Ala Ser Pro Asn Tyr Ala Leu Met Ile Tyr Asp Gly
305                 310                 315                 320

Asp Gly Ser Ala Phe Asn Gln Ser Gly Pro Ala Gly Ser Ala Gln Ile
            325                 330                 335

Glu Lys Leu Phe Glu Asp Tyr Tyr Asp Ser Ile Asp Leu Pro His Ile
            340                 345                 350

Pro Thr Gln Phe Asp Gly Arg Ser Asp Tyr Glu Ala Phe Ile Leu Asn
            355                 360                 365

Gly Ile Pro Ala Gly Gly Leu Phe Thr Gly Ala Glu Gly Ile Met Ser
            370                 375                 380

Glu Glu Asn Ala Ser Arg Trp Gly Gln Ala Gly Val Ala Tyr Asp
385                 390                 395                 400

Ala Asn Tyr His Ala Val Gly Asp Asn Met Thr Asn Leu Asn His Glu
            405                 410                 415

Ala Phe Leu Ile Asn Ser Lys Ala Thr Ala Phe Ala Val Ala Thr Tyr
            420                 425                 430

Ala Asn Asp Leu Ser Ser Ile Pro Lys Arg Asn Thr Thr Ser Ser Leu
            435                 440                 445

His Arg Arg Ala Arg Thr Met Arg Pro Phe Gly Lys Arg Ala Pro Lys
            450                 455                 460

Thr His Ala His Val Ser Gly Ser Gly Cys Trp His Ser Gln Val Glu
465                 470                 475                 480

Ala
```

SEQ ID NO:2:

```
atgaggtcgc tttatgggc  ttcgttgctt  cggggcgt   tggctgggag ggcgcttgtt  60
tcgccggttc gttttttct  tcttttcttt  gcgattctgg tcttttttga ttgcttttct  120
tgagcttggg tgttaagtgt tgagtgttga ctgagctaat gttatgtcta ggatgagttc  180
ccagaggata tccagttgga agatctgctg gaaggatccc aacagctcga ggactttgcc  240
tatgcctacc ccgagcgcaa tcgcgtcttt ggtggtaaag cccacgacga cacggtcaac  300
tacctctaca aggagctgaa gaagactggc tactacgatg tctacaagca gccccaggtc  360
cacctgtgga gcaatgccga ccagacgctc aaggtgggcg acgaggaaat cgaggcgaag  420
accatgacct atagtcccag cgtcgaagta actgccgatg tagccgtcgt caagaacctg  480
ggatgcagtg aggcggatta ccatccgat  gtcgagggca aggtagctct catcaagcgt  540
ggagaatgtg cgttcggcga caagtcggtt ctcgctgcca aagccaaggc cgcggcttcg  600
```

-continued

```
attgtctata acaatgtggc aggatccatg gcaggcaccc ttggcgcggc gcagagtgac    660
aaggaccgta attcggccat tgtcggtatc agcttggagg atggccagaa gctgatcaag    720
cttgctgagg ctggatcggt atctgtggat ctgtgggtgg atagcaagca ggagaaccgt    780
acgacgtata acgttatcgc gcagacgaag ggcggcgatc cgaacaatgt cgtcgcgctg    840
ggtggccaca ctgactcggt cgaggcgggc cctggtatca atgacgatgg ctcgggcatt    900
attagcaacc tggtcgttgc caaagcgctg acgcagtact ccgtcaagaa tgccgtgcgc    960
tttctcttct ggacggccga ggagttcggt ctcctgggca gcaactacta cgtctcccat   1020
ctgaatgcca ccgagctgaa caagatcaga ctgtacctga acttcgacat gatcgcctcg   1080
cccaactacg ccctcatgat ctatgacggt gacggatcgg cgttcaacca gagcggaccg   1140
gccggatccg cccagatcga gaaactgttc gaggactact acgactccat cgacttgcct   1200
catatcccga cccagttcga cggacgttcc gattacgagg cctttatcct gaacggcatt   1260
ccggccggtg gactcttcac gggcgccgag ggcatcatgt ccgaagagaa cgcaagccgt   1320
tgggagggtc aagccggcgt ggcctacgac gccaactacc acgccgtggg agacaacatg   1380
accaacctca accatgaagc cttcctgatc aactccaaag ccacagcctt cgccgtcgcc   144d acctacgcca acgacctatc ctcgatcccc aaacggaata ccacatcctc tctgcaccga   1500
cgagcccgca ccatgcgacc attcgggaaa agagctccga agacgcacgc tcacgtatca   1560
ggatccggat gctggcattc tcaagttgag gcatagatcg ataggtaaag accgactctt   1620
acatagtaag gcctgtagga                                                1640
```

---

What is claimed is:

1. An isolated leucine aminopeptidase polynucleotide encoding a protein having an amino acid sequence shown in SEQ ID NO1.

2. An isolated leucine aminopeptidase polynucleotide comprising a DNA having a nucleotide sequence shown in SEQ ID NO:2.

3. A recombinant DNA, wherein the isolated leucine aminopeptidase polynucleotide of claim 1 or 2 has been inserted into a vector DNA.

4. A host cell transformant transformed with the DNA containing the isolated leucine aminopeptidase polynucleotide of claim 1 or 2.

5. A host cell transformed with the recombinant DNA of claim 3.

6. A process for producing leucine aminopeptidase, comprising the steps of:

culturing the host cell of claim 4 in a medium; and recovering leucine aminopeptidase from the medium.

7. A process for producing leucine aminopeptidase, comprising the steps of:

culturing the host cell of claim 5 in a medium; and
recovering leucine aminopeptidase from the medium.

* * * * *

SEQUENCE LISTING

<160> NUMBER OF SEQ ID NOS: 14

<210> SEQ ID NO 1
<211> LENGTH: 481
<212> TYPE: PRT
<213> ORGANISM: Aspergillus sojae

<400> SEQUENCE: 1

```
Gly Arg Ala Leu Val Ser Pro Asp Glu Phe Pro Glu Asp Ile Gln Leu
  1               5                  10                  15

Glu Asp Leu Leu Glu Gly Ser Gln Gln Leu Glu Asp Phe Ala Tyr Ala
             20                  25                  30

Tyr Pro Glu Arg Asn Arg Val Phe Gly Gly Lys Ala His Asp Asp Thr
         35                  40                  45

Val Asn Tyr Leu Tyr Lys Glu Leu Lys Lys Thr Gly Tyr Tyr Asp Val
     50                  55                  60

Tyr Lys Gln Pro Gln Val His Leu Trp Ser Asn Ala Asp Gln Thr Leu
 65                  70                  75                  80

Lys Val Gly Asp Glu Glu Ile Glu Ala Lys Thr Met Thr Tyr Ser Pro
                 85                  90                  95

Ser Val Glu Val Thr Ala Asp Val Ala Val Lys Asn Leu Gly Cys
            100                 105                 110

Ser Glu Ala Asp Tyr Pro Ser Asp Val Glu Gly Lys Val Ala Leu Ile
        115                 120                 125

Lys Arg Gly Glu Cys Ala Phe Gly Asp Lys Ser Val Leu Ala Ala Lys
    130                 135                 140
```

```
Ala Lys Ala Ala Ala Ser Ile Val Tyr Asn Asn Val Ala Gly Ser Met
145                 150                 155                 160

Ala Gly Thr Leu Gly Ala Ala Gln Ser Asp Lys Gly Pro Tyr Ser Ala
            165                 170                 175

Ile Val Gly Ile Ser Leu Glu Asp Gly Gln Lys Leu Ile Lys Leu Ala
            180                 185                 190

Glu Ala Gly Ser Val Ser Val Asp Leu Trp Val Asp Ser Lys Gln Glu
            195                 200                 205

Asn Arg Thr Thr Tyr Asn Val Ile Ala Gln Thr Lys Gly Gly Asp Pro
210                 215                 220

Asn Asn Val Val Ala Leu Gly His Thr Asp Ser Val Glu Ala Gly
225                 230                 235                 240

Pro Gly Ile Asn Asp Asp Gly Ser Gly Ile Ile Ser Asn Leu Val Val
            245                 250                 255

Ala Lys Ala Leu Thr Gln Tyr Ser Val Lys Asn Ala Val Arg Phe Leu
            260                 265                 270

Phe Trp Thr Ala Glu Glu Phe Gly Leu Leu Gly Ser Asn Tyr Tyr Val
            275                 280                 285

Ser His Leu Asn Ala Thr Glu Leu Asn Lys Ile Arg Leu Tyr Leu Asn
290                 295                 300

Phe Asp Met Ile Ala Ser Pro Asn Tyr Ala Leu Met Ile Tyr Asp Gly
305                 310                 315                 320

Asp Gly Ser Ala Phe Asn Gln Ser Gly Pro Ala Gly Ser Ala Gln Ile
            325                 330                 335

Glu Lys Leu Phe Glu Asp Tyr Tyr Asp Ser Ile Asp Leu Pro His Ile
            340                 345                 350

Pro Thr Gln Phe Asp Gly Arg Ser Asp Tyr Glu Ala Phe Ile Leu Asn
            355                 360                 365

Gly Ile Pro Ala Gly Gly Leu Phe Thr Gly Ala Glu Gly Ile Met Ser
            370                 375                 380

Glu Glu Asn Ala Ser Arg Trp Gly Gln Ala Gly Val Ala Tyr Asp
385                 390                 395                 400

Ala Asn Tyr His Ala Val Gly Asp Asn Met Thr Asn Leu Asn His Glu
            405                 410                 415

Ala Phe Leu Ile Asn Ser Lys Ala Thr Ala Phe Ala Val Ala Thr Tyr
            420                 425                 430

Ala Asn Asp Leu Ser Ser Ile Pro Lys Arg Asn Thr Thr Ser Ser Leu
            435                 440                 445

His Arg Arg Ala Arg Thr Met Arg Pro Phe Gly Lys Arg Ala Pro Lys
450                 455                 460

Thr His Ala His Val Ser Gly Ser Gly Cys Trp His Ser Gln Val Glu
465                 470                 475                 480

Ala

<210> SEQ ID NO 2
<211> LENGTH: 1640
<212> TYPE: DNA
<213> ORGANISM: Aspergillus sojae

<400> SEQUENCE: 2
atgaggtcgc tttttatgggc ttcgttgctt cgggggcgt tggctgggag ggcgcttgtt      60
tcgccggttc gttttttttct tcttttcttt gcgattctgg tcttttttga ttgcttttct    120
tgagcttggg tgttaagtgt tgagtgttga ctgagctaat gttatgtcta ggatgagttc    180
```

-continued

```
ccagaggata tccagttgga agatctgctg gaaggatccc aacagctcga ggactttgcc      240
tatgcctacc ccgagcgcaa tcgcgtcttt ggtggtaaag cccacgacga cacggtcaac      300
tacctctaca aggagctgaa gaagactggc tactacgatg tctacaagca gccccaggtc      360
cacctgtgga gcaatgccga ccagacgctc aaggtgggcg acgaggaaat cgaggcgaag      420
accatgacct atagtcccag cgtcgaagta actgccgatg tagccgtcgt caagaacctg      480
ggatgcagtg aggcggatta ccatccgat gtcgagggca aggtagctct catcaagcgt      540
ggagaatgtg cgttcggcga caagtcggtt ctcgctgcca agccaaggc cgcggcttcg       600 attgtctata caatgtggc aggatccatg gcaggcaccc ttggcgcggc gcagagtgac      660
aaggaccgta attcggccat tgtcggtatc agcttggagg atggccagaa gctgatcaag      720
cttgctgagg ctggatcggt atctgtggat ctgtgggtgg atagcaagca ggagaaccgt      780
acgacgtata acgttatcgc gcagacgaag ggcggcgatc cgaacaatgt cgtcgcgctg      840
ggtggccaca ctgactcggt cgaggcgggc cctggtatca atgacgatgg ctcgggcatt      900
attagcaacc tggtcgttgc caaagcgctg acgcagtact ccgtcaagaa tgccgtgcgc      960
tttctcttct ggacggccga ggagttcggt ctcctgggca gcaactacta cgtctcccat     1020
ctgaatgcca ccgagctgaa caagatcaga ctgtacctga acttcgacat gatcgcctcg     1080
cccaactacg ccctcatgat ctatgacggt gacggatcgg cgttcaacca gagcggaccg     1140
gccggatccg cccagatcga gaactgttc gaggactact acgactccat cgacttgcct      1200
catatcccga cccagttcga cggacgttcc gattacgagg ccttatcct gaacggcatt      1260 ccggccggtg gactcttcac gggcgccgag ggcatcatgt ccgaagagaa cgcaagccgt     1320
tggggaggtc aagccggcgt ggcctacgac gccaactacc acgccgtggg agacaacatg     1380
accaacctca accatgaagc cttcctgatc aactccaaag ccacagcctt cgccgtcgcc     1440
acctacgcca cgacctatc ctcgatcccc aaacggaata ccacatcctc tctgcaccga      1500
cgagcccgca ccatgcgacc attcgggaaa agagctccga agacgcacgc tcacgtatca     1560
ggatccggat gctggcattc tcaagttgag gcatagatcg ataggtaaag accgactctt     1620
acatagtaag gcctgtagga                                                 1640
```

```
<210> SEQ ID NO 3
<211> LENGTH: 11
<212> TYPE: PRT
<213> ORGANISM: Aspergillus sojae

<400> SEQUENCE: 3

Gly Arg Ala Leu Val Ser Pro Asp Glu Phe Pro
 1               5                  10

<210> SEQ ID NO 4
<211> LENGTH: 15
<212> TYPE: PRT
<213> ORGANISM: Aspergillus sojae
<220> FEATURE:
<223> OTHER INFORMATION: Xaa is an amino acid that was unable to
      be identified.

<400> SEQUENCE: 4

Xaa Xaa Xaa Xaa Xaa Xaa Xaa Asp Tyr Pro Ser Val Glu Gly Lys
 1               5                  10                  15

<210> SEQ ID NO 5
<211> LENGTH: 7
<212> TYPE: PRT
```

```
<213> ORGANISM: Aspergillus sojae

<400> SEQUENCE: 5

Gln Pro Gln Val His Leu Trp
 1               5

<210> SEQ ID NO 6
<211> LENGTH: 25
<212> TYPE: PRT
<213> ORGANISM: Aspergillus sojae

<400> SEQUENCE: 6

Asn Ala Val Arg Phe Leu Phe Trp Thr Ala Glu Glu Phe Gly Leu Leu
 1               5                  10                  15

Gly Ser Asn Tyr Tyr Val Ser His Leu
            20                  25

<210> SEQ ID NO 7
<211> LENGTH: 27
<212> TYPE: DNA
<213> ORGANISM: Artificial sequence
<220> FEATURE:
<223> OTHER INFORMATION: n = inosine
<220> FEATURE:
<223> OTHER INFORMATION: Designated is a PCR primer for amplifying
      part of the leucine aminopeptidase gene from Aspergillus sojae.

<400> SEQUENCE: 7
gaytayccnw sngaygtnga rggnaag                                          27

<210> SEQ ID NO 8
<211> LENGTH: 26
<212> TYPE: DNA
<213> ORGANISM: Artificial sequence
<220> FEATURE:
<223> OTHER INFORMATION: n = inosine
<220> FEATURE:
<223> OTHER INFORMATION: Designated is a PCR primer for amplifying
      part of the leucine aminopeptidase gene from Aspergillus sojae.

<400> SEQUENCE: 8
ttnccytcna crtcnswngg rtartc                                           26

<210> SEQ ID NO 9
<211> LENGTH: 23
<212> TYPE: DNA
<213> ORGANISM: Artificial sequence
<220> FEATURE:
<223> OTHER INFORMATION: n = inosine
<220> FEATURE:
<223> OTHER INFORMATION: Designated is a PCR primer for amplifying
      part of the leucine aminopeptidase gene from Aspergillus sojae.

<400> SEQUENCE: 9
ttytggacng cngargartt ygg                                              23

<210> SEQ ID NO 10
<211> LENGTH: 23
<212> TYPE: DNA
<213> ORGANISM: Artificial sequence
<220> FEATURE:
<223> OTHER INFORMATION: n = inosine
<220> FEATURE:
<223> OTHER INFORMATION: Designated is a PCR primer for amplifying
      part of the leucine aminopeptidase gene from Aspergillus sojae.

<400> SEQUENCE: 10
```

-continued

```
ccraaytcyt cngcngtcca raa                                    23

<210> SEQ ID NO 11
<211> LENGTH: 28
<212> TYPE: DNA
<213> ORGANISM: Aspergillus sojae

<400> SEQUENCE: 11
agggcaaggt agctctcatc aagcgtgg                               28

<210> SEQ ID NO 12
<211> LENGTH: 28
<212> TYPE: DNA
<213> ORGANISM: Aspergillus sojae

<400> SEQUENCE: 12
gagaaagcgc acggcattct tgacggag                               28

<210> SEQ ID NO 13
<211> LENGTH: 24
<212> TYPE: DNA
<213> ORGANISM: Artificial sequence
<220> FEATURE:
<223> OTHER INFORMATION: Designated is a PCR primer capable of
      annealing with a cloning site of the plasmid pLZA or pLZD.

<400> SEQUENCE: 13
cgacgttgta aaacgacggc cagt                                   24

<210> SEQ ID NO 14
<211> LENGTH: 24
<212> TYPE: DNA
<213> ORGANISM: Artificial sequence
<220> FEATURE:
<223> OTHER INFORMATION: Designated is a PCR primer capable of
      annealing with a cloning site of the plasmid pLZA or pLZD.

<400> SEQUENCE: 14
gagcggataa caatttcaca cagg                                   24
```